United States Patent [19]

Chimenti et al.

[11] Patent Number: 4,674,334

[45] Date of Patent: Jun. 23, 1987

[54] PROPERTIES OF COMPOSITE LAMINATES USING LEAKY LAMB WAVES

[75] Inventors: Dale E. Chimenti, Centerville, Ohio; Yoseph Bar-Cohen, Seal Beach, Calif.

[73] Assignee: The United States of America as represented by the Secretary of the Air Force, Washington, D.C.

[21] Appl. No.: 865,507

[22] Filed: May 13, 1986

[51] Int. Cl.[4] ............................................. G01N 29/04
[52] U.S. Cl. ........................................ 73/627; 73/628; 73/644
[58] Field of Search ................. 73/644, 627, 628, 641, 73/DIG. 1

[56] References Cited

U.S. PATENT DOCUMENTS

| | | | |
|---|---|---|---|
| 3,165,922 | 1/1965 | Worlton | 73/627 |
| 3,250,120 | 5/1966 | Dickinson, III | 73/627 |
| 3,512,400 | 5/1970 | Lynnworth | 73/597 |
| 4,182,155 | 1/1980 | Fowler | 73/1 DV |
| 4,457,174 | 7/1984 | Bar-Cohen et al. | 73/598 |
| 4,494,408 | 1/1985 | DeLacy | 73/587 |
| 4,523,468 | 6/1985 | Derkacs et al. | 73/598 |
| 4,538,462 | 9/1985 | Hartog et al. | 73/577 |
| 4,558,598 | 12/1985 | Young | 73/644 |

*Primary Examiner*—Anthony V. Ciarlante
*Attorney, Agent, or Firm*—Bobby D. Scearce; Donald J. Singer

[57] ABSTRACT

Method and system for detecting defects in the structure of a composite laminate material are described which comprise a first transducer for directing an ultrasonic beam of preselected frequency along a transmission axis onto a surface of the laminate at a preselected angle to generate Lamb waves in the laminate and leaky Lamb waves reflected therefrom; a second transducer for detecting the reflected leaky Lamb waves and for providing an output signal corresponding to the amplitude of the reflected waves; a fluid sonically coupling the laminate with the transducers; a positioning system for selectively positioning the transducers along the surface of the laminate to produce a set of output signals characterizing the laminate; and suitable electronics for receiving and processing the output signals and comparing them with signals characteristic of a defect free sample of the laminate.

15 Claims, 9 Drawing Figures

U.S. Patent    Jun. 23, 1987    Sheet 1 of 4    4,674,334
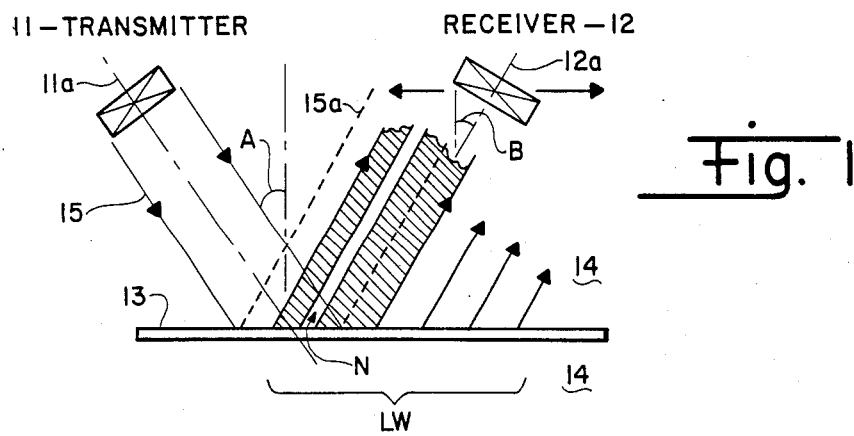
Fig. 1
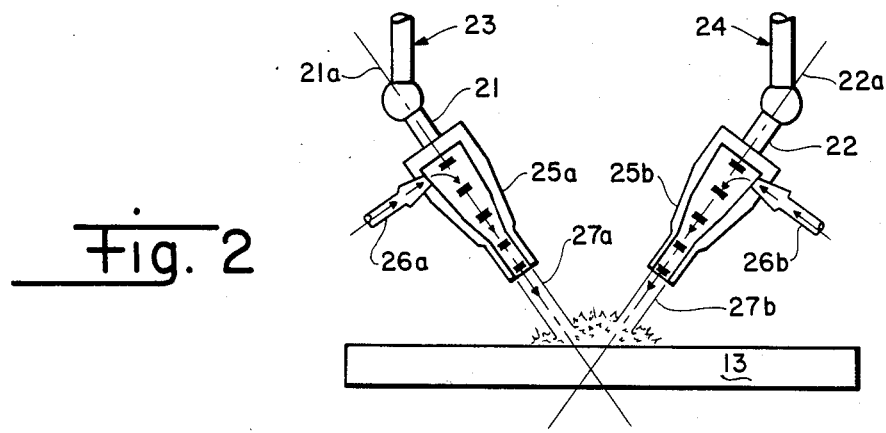
Fig. 2
Fig. 7
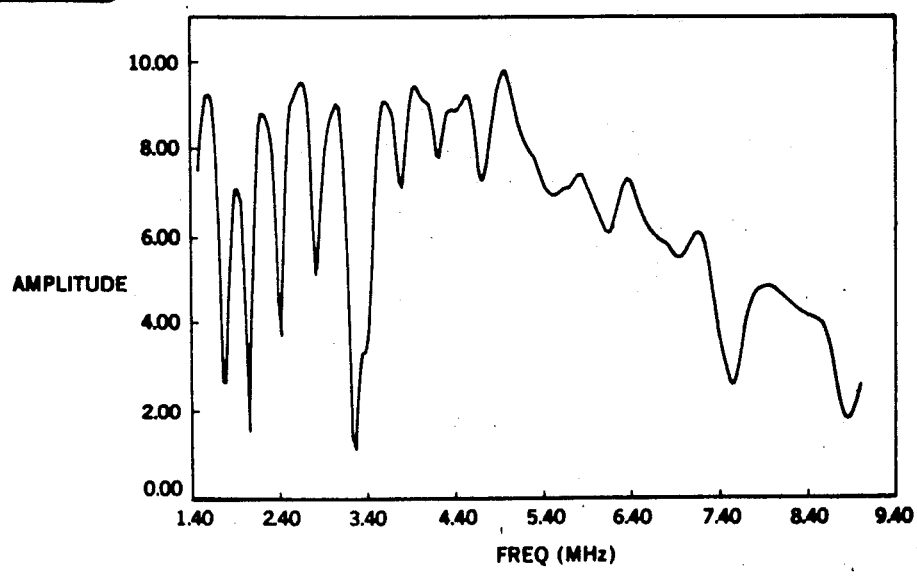

PROPERTIES OF COMPOSITE LAMINATES USING LEAKY LAMB WAVES

RIGHTS OF THE GOVERNMENT

The invention described herein may be manufactured and used by or for the Governement of the United States for all governmental purposes without the payment of any royalty.

BACKGROUND OF THE INVENTION

The invention relates generally to nondestructive testing methods for composite materials, and more particularly to method and system for nondestructive evaluation of composite laminates.

Composite materials, particularly fibrous composite laminates, are of substantial interest to the aerospace industry for aircraft structural components by reason of high strength-to-weight ratios which characterize these materaials. In fabricating composite laminates, numerous performance limiting defects may arise within the laminate structure, including delaminations, porosity, voids, ply gaps and overlaps, resin rich and resin starved regions, fiber misalignment, and cracks. Certain defects not detected in the laminate structure as manufactured may arise in the material during use. Nondestructive testing (NDT) methods are presently used to detect the defects and include x-ray radiography and ultrasonics in various modes such as pulse echo and through transmission. However, the nonhomogeneous anisotropic structure which characterizes fibrous composites severely limits the suitability of conventional methods for nondestructive evaluation of these materials.

The invention eliminates or substantially reduces in critical importance the aforesaid shortcomings in the nondestructive testing art by providing a novel method using leaky Lamb waves to detect and characterize defects in fibrous composite laminates, which defects may not be detectable using conventional NDT techniques. Based on a clear understanding of ultrasonic wave propagation in composite laminate materials, the method of the invention allows detection of defects utilizing plate (Lamb) waves in fluid-loaded, fibrous composite materials. In practicing the method of the invention, leaky Lamb waves are excited in water coupled composite laminate plates by ultrasonic insonification at appropriate angles and frequencies using a two-transducer, pitch-catch geometry. The method takes advantage of the physical distortion in the reflected field, which occurs only at discrete leaky wave conditions, to enhance signal-to-noise ratios of ultrasonic energy reflected from a composite plate. Insertion and extraction of leaky Lamb waves in composites is done by immersing the transducers and plate in a sound coupling fluid (water) or by using two captured water columns which couple the transducers and plate.

The invention is therefore useful for nondestructive evaluation of substantially any plate material, and is of particular utility for the detection and characterization of porosity and other defects in structural composite laminates. The method of the invention has clear superiority over conventional techniques, such as the pulse echo technique, in the detection of dilute porosity, and may find broad application in manufacturing quality assurance inspections.

It is, therefore, a principle object of the invention to provide novel nondestructive evaluation method and system.

It is a further object of the invention to provide method and system for nondestructively testing composite materials.

It is another object of the invention to provide nondestructive testing method and system utilizing leaky Lamb waves.

These and other objects of the invention will become apparent as the detailed description of representative embodiments proceeds.

SUMMARY OF THE INVENTION

In accordance with the foregoing principles and objects of the invention, novel method and system for detecting defects in the structure of a composite laminate material are described which comprise a first transducer for directing an ultrasonic beam of preselected frequency along a transmission axis onto a surface of the laminate at preselected angle to generate Lamb waves in the laminate and leaky Lamb waves reflected therefrom; a second transducer for detecting the reflected leaky Lamb waves and for providing an output signal corresponding to the amplitude of the reflected waves; a fluid sonically coupling the laminate with the transducers; a positioning system for selectively positioning the transducers along the surface of the laminate to produce a set of output signals characterizing the laminate; and suitable electronics for receiving and processing the output signals and comparing them with signals characteristic of a defect free sample of the laminate.

DESCRIPTION OF THE DRAWINGS

The invention will be more clearly understood from the following detailed description of representative embodiments thereof read in conjunction with the accompanying drawings wherein:

FIG. 1 is a schematic of the system used in the generation and detection of leaky Lamb waves according to the invention;

FIG. 2 is a drawing of a transducer setup for captured water column operation according to the invention;

FIG. 7 shows the leaky Lamb wave spectral response of a sample of graphite/epoxy laminate AS4/3501-6$[0]_{32}$ showing porosity.

DETAILED DESCRIPTION

Figure 3:
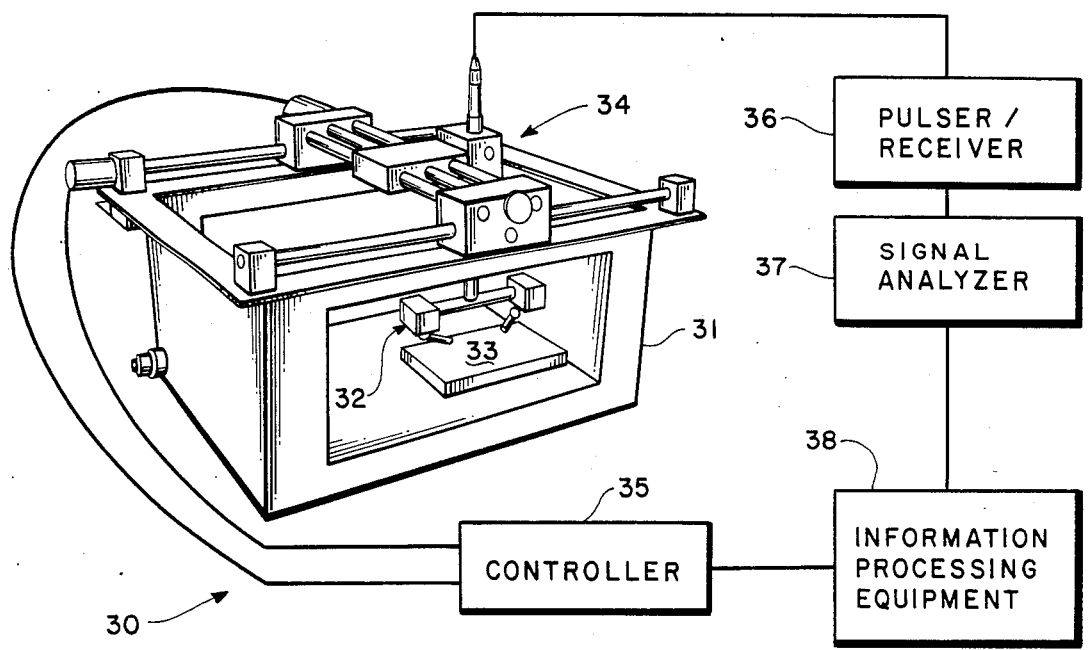
FIG. 3 is a schematic of a representative system for testing composite laminates according to the invention.

Theoretical discussions on layered and fibrous composite models and experimental measurements in consideration of the invention are detailed in a separate publication ("Leaky Lamb Waves in Fibrous Composite Laminates", by D. E. Chimenti and A. H. Nayfeh, J Appl Phys 58:12, 4531–38 (Dec. 15, 1985)), the same being incorporated by reference herein.

Referring now to FIG. 1, shown therein is a schematic of a system for leaky Lamb wave generation and detection in the composite testing method of the invention. As suggested in FIG. 1, two ultrasonic transducers 11,12 are positioned above a composite sample in the form of plate 13 to be examined. Transducers 11,12 and plate 13 are submerged in a suitable sound coupling fluid 14, such as water. Transducers 11,12 are oriented above plate 13 such that the respective principal wave propagagion axes 11a,12a thereof define a plane perpendicular to plate 13 and intersect at a preselected point below the upper surface of plate 13. In the system of FIG. 1 transducer 11 is the transmitter and transducer 12 is the receiver. Transducers 11,12 are movable relative to each other and relative to and along the upper surface of plate 13 in order to position the sonic propagation axes 11a,12a at appropriate angles for generation and detection of leaky Lamb waves. Transmitter transducer 11 is oriented so that axis 11a of propagation of energy therefrom defines an angle A with a normal to the upper surface of plate 13 of about 8° to 75°. Axis 12a of transducer 12 is oriented at corresponding angle B of about 8° to 75° relative to a normal to plate 13. The angle of incidence of ultrasonic energy from transducer 11 depends on several factors including the elastic properties of the laminate material, and is therefore not limiting of the invention, although it was found in inspecting various laminate plates in demonstration of the method of the invention that, for practical purposes and in consideration of the capabilities of available equipment, the stated range is suitable and preferable.

As suggested in the diagram of FIG. 1, transducer 11 transmits ultrasonic energy via beam 15 along axis 11a at the preselected angle A. Ultrasonic frequencies in the range of about 0.5 to 15.0 MHz were found suitable in examiniation of composite laminates in the practice of the invention, depending on the specific material being examined. Any specular reflection of beam 15 from the surface of plate 13 is defined by dashed lines 15a. The reflected acoustic field that characterizes the leaky Lamb wave phenomenon is also illustrated in FIG. 1. At ultrasonic frequencies and transducer geometry admitting to generation of Lamb waves in plate 13, the reflected ultrasonic field shows the displacement and distortion characteristic of the presence of Lamb waves propagating along the plate. Leaky Lamb waves generated by the interaction of beam 15 with plate 13 are represented by the shaded region and the arrows in FIG. 1 in the region bearing the legend LW. Interaction of reflected components leads, under favorable conditions of sound wavelength and beam width, to a phase cancellation which is mainifested as a characteristic null zone N located substantially as shown. The phase cancellation phenomenon which distorts the reflected beam only occurs within a fairly narrow range of sound wavelength and beam width. Further, it depends on the value of the leaky wave coupling parameter, which itself is dependent on material constants and angle of incidence, but not on the frequency. While the beam distortion (i.e., phase cancellation) effect does enhance the detectability of the leaky Lamb wave, it is not essential to the observation of the phenomenon. Once a leaky Lamb wave is identified in a known defect free sample plate, an appropriate scan is set up at a selected frequency with the transducers oriented to observe null zone N. The signal level at null zone N provides a very sensitive measure of variations in the structure of plate 13 resulting from local change of properties or from discontinuities and defects. Not illustrated in FIG. 1 is the transmitted field below plate 13 which will contain most of the energy from beam 15.

As suggested above, sound coupling must be efected between transducers 11,12 and plate 13 as by submersion in sound coupling fluid 14. Alternatively, however, the arrangement shown in FIG. 2 may be utilized to couple the transducers and plate, wherein the transducers are configured for captured water column operation. It is first noted that Lamb waves, once excited in plate 13, are leaky only so long as plate 13 is in contact with the fluid (viz, water), that is, the fluid depth is large compared to the thickness of plate 13. Accordingly, in the arrangement of FIG. 2, transducers 21,22 may be attached to respective manipulator arms 23,24 substantially as shown for operative interconnection to a system such as described below in relation to FIG. 3. Transducers 21,22 have attached thereto respective nozzles 25a,25b having fluid (water) inlets 26a,26b for directing water onto plate 13 in a pair of water columns 27a,27b directed along the respective transducer axes 21a,22a. If water columns 27a,27b (and sound propagation axes 21a,22a) are oriented so that ultrasonic energy is incident on plate 13 as depicted in FIG. 2, leaky Lamb waves will be generated, but energy leakage from the Lamb waves will occur only where water columns 27a,27b make contact with plate 13. Accordingly, in the configuration of FIG. 2, the placement of transducers 21,22 is less critical, and water columns 27a,27b may be separated by a larger distance than that between the intersection of axes 11a,12a with plate 13 in an immersion setup (FIG. 1). The water column arrangement therefore allows inspection of a larger area of plate 13 in one scan than for the arrangement of FIG. 1, and further allows manual inspection of plates.

Referring to FIG. 3, shown therein is a drawing of a representative system 30 useful in practicing the method of the invention. System 30 comprises a housing 31 for supporting transducer assembly 32, such as those described as including transducers 11,12 or 21,22 of FIGS. 1 or 2, and for suitably enclosing and supporting composite laminate plate 33 for test. Housing 31 may be substantially closed in order to contain the fluid bath for sonically coupling the transducers and plate, or may be otherwise equipped with fluid inlet and outlet for providing fluid (water) to the transducer assembly 32 if configured for captured water column operation (ref FIG. 2). A two or three dimensional positioning system 34 operatively connected to controller 35 provides means for controllably positioning transducer assembly 32 over plate 33 in performing a scan of plate 33 (i.e., such as a C-scan wherein both transducers are scanned in tandem fashion over the area of and at constant height from the test plate; signals from the receiver are monitored to generate an x-y display which represents the internal structure (i.e., defects, property variations) of the test plate). Pulser/receiver 36 and signal analyzer 37 are operatively connected to the transducers for receiving and processing signals from transducer assembly 32. Information processing equipment 38 acquires, processes, stores and displays information in response to controller 35 and signal analyzer 37 and programs their operation in the practice of the invention.

Referring again to FIG. 1, each transducer 11,12 is positioned a distance above plate 13 corresponding to several transducer diameters (5 to 10 cm in the FIG. 1 arrangement) and sufficient to place plate 13 in the radiation farfield of transducers 11,12. Propagation axes 11a,12a must intersect at a point below the upper surface of plate 13 a preselected distance (usually in the range of 0.2 to 0.8 cm) which is chosen to yield the strongest amplitude extinction of the reradiated signal at those discrete frequencies (depending on plate thickness and elastic constants) where leaky Lamb waves are generated. This is an important feature of the invention and exploits the phase cancellation of portions of the reradiated signal where mode conversion to the leaky Lamb waves occurs, to enhance defect detectability. Because the wave is leaky, spatial localization of energy in the reflected wave is high which results in good resolution without focusing the beam. Variations in the reflected signal correspond to changes in plate 13 properites which may be related to the presence of a defect.

Figure 4:
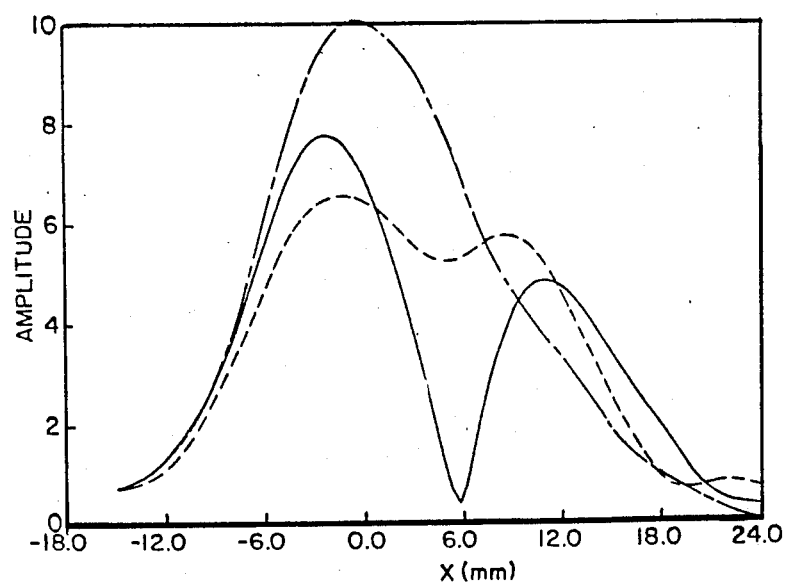
FIG. 4 is a profile of a reflected beam at and near the Lamb angle for a 1.14-mm glass-epoxy plate in water.

The phase cancellation effect as observed in the reradiated field is illustrated in FIG. 4, which is a profile of a reflected beam at and near the Lamb angle for a composite plate of 1.14-mm glass-epoxy in water. FIG. 4 shows a plot of the amplitude of the reflected field as a function of transducer 12 (receiver) position scanned parallel to the surface of plate 13 for an incidence angle A of 18° (ref FIG. 1). Solid curve 41 illustrates satisfaction of the Lamb condition corresponding to 2.19 MHz. Broken line 42 represents the profile at a frequency 200 kHz above the Lamb condition, and dashed line 43 represents the profile at a frequency 200 kHz below the Lamb condition. The reflected field in FIG. 4 displays the strong distortion and spatial displacement described above. Varying the frequency by 10% in either direction results in beam profiles more closely approximating the incident beam. Away from the resonance condition for efficient mode conversion from a compressional wave in the fluid to a Lamb wave in the plate, ultrasonic reflection is nearly specular. A feature of the method of the invention is the observation of nonspecular reflection at angles and frequencies of strong mode conversion which enhance detectability of Lamb waves in the plate by placing the receiver transducer at a position corresponding to the strong minimum in the beam profile. For example, in the illustration of FIG. 3, defects may be detected by scanning the surface of plate 33 with transducer assembly 32, or alternativley, moving plate 33 under the transducers, keeping the transducer-plate distance constant. The presence of a defect will significantly change the excitation of some or all of the leaky Lamb wave modes as compared to a defect free plate, depending on the type and spatial extent of the defect within plate 33.

Several example scans were made to demonstrate the utility of the method of the invention. Measurements on graphite/epoxy composite laminates were made at incidence angles of about 20° using for simplicity of demonstration unidirectional laminates with Lamb wave propagation along the fiber direction. It is understood that the principles of the invention may be extended to other laminated structures and wave propagation directions, the same being contemplated within the scope of these teachings.

Figure 5A:
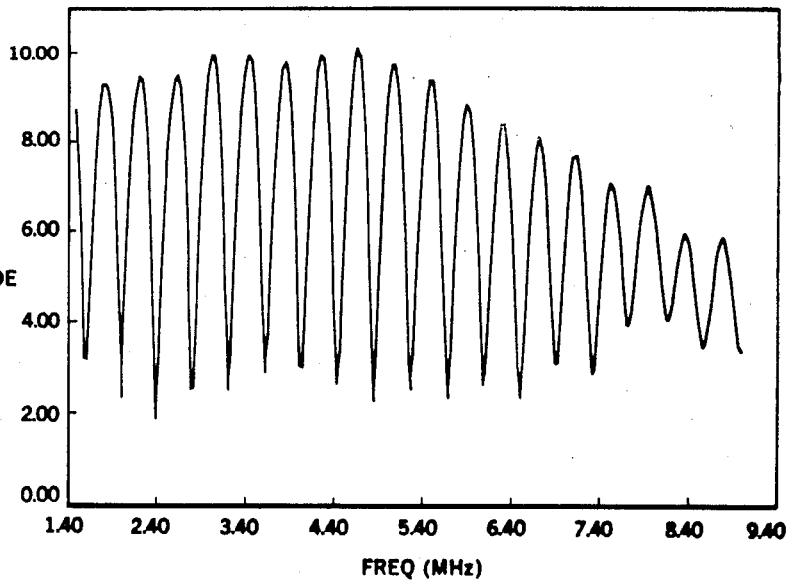
FIG. 5a shows the leaky Lamb wave spectral response for a defect free composite sample of graphite/epoxy AS4/3501-6$[0]_{32}$.
Figure 5B:
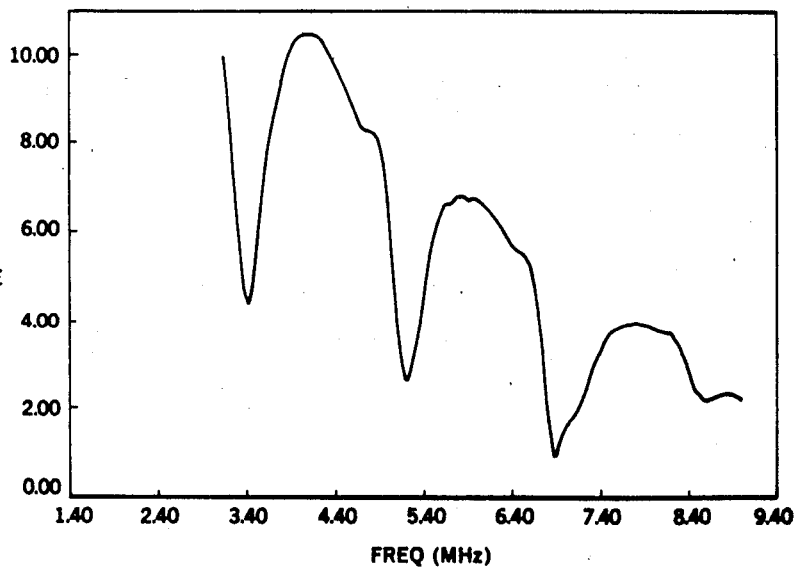
FIG. 5b shows the leaky Lamb wave spectral response for a sample of graphite/epoxy AS4/3501-6$[0]_{32}$ having delaminations.

FIG. 5a shows the reflection spectra for leaky Lamb waves in a defect free sample plate of graphite/epoxy AS4/3501-6[0]$_{32}$ tested at 22° along the fibers of the laminate. The pronounced minima in the frequency response trace of FIG. 5a indicate the presence of leaky Lamb wave modes in the plate at each corresponding frequency. The spectral response for a sample of defect free material establishes a base from which deviations will appear as spatially varying material properties (i.e., defects) in a test composite plate. The type of defect will determine which exitation mode is reduced. FIG 5b shows the reflection spectra for the material of FIG. 5a having known delaminations built into the laminate, by embedding Teflon$^R$ wafers between preselected layers of the laminate during layup. The trace of FIG. 5b (known delaminations between layers 8 and 9 of the laminate) clearly suggests the presence of the defect.

Figure 6A:
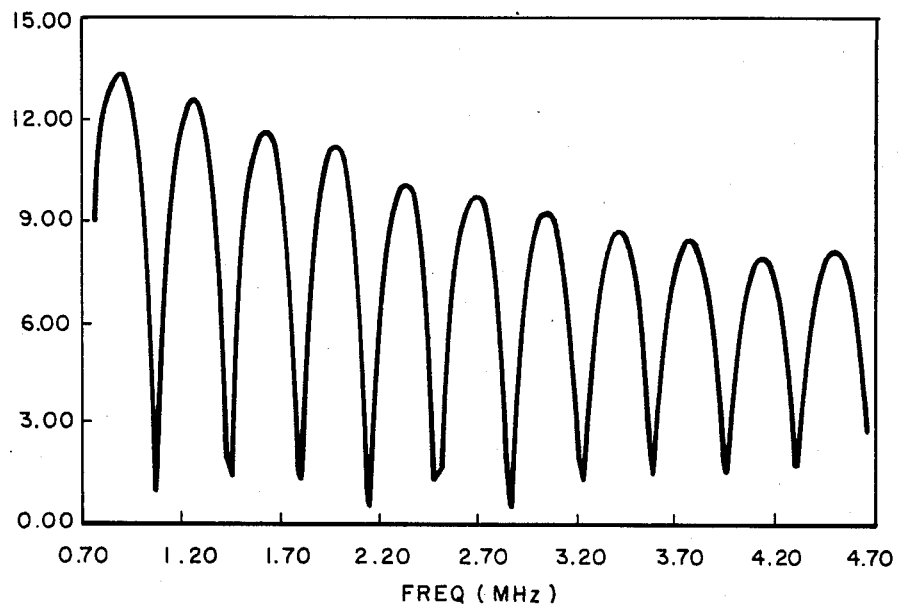
FIG. 6a shows the leaky Lamb wave spectral response for a defect free composite sample of graphite/epoxy T300/CG914$[0]_{24}$.
Figure 6B:
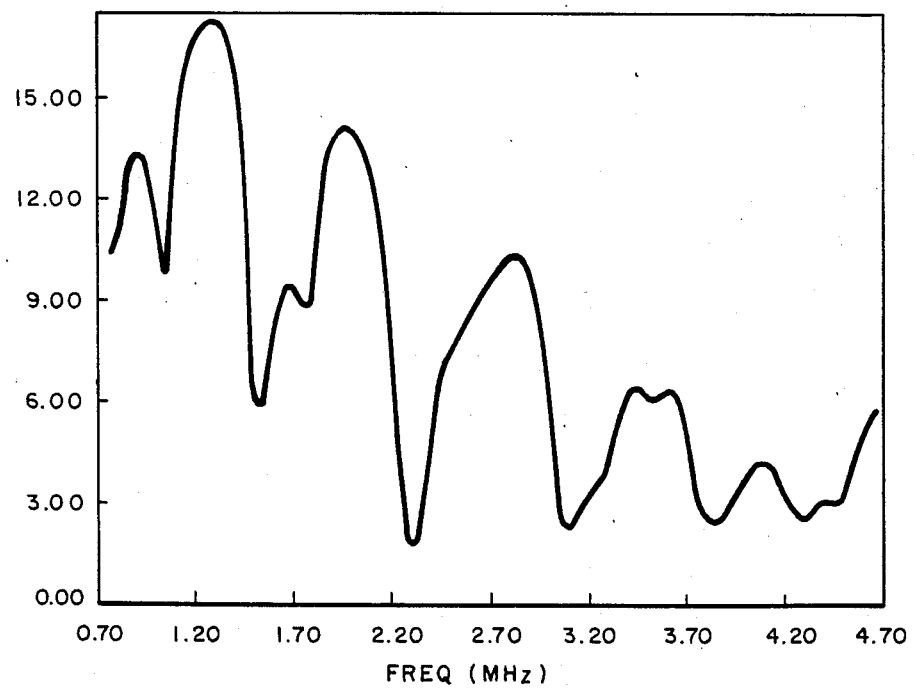
FIG. 6b shows the leaky Lamb wave spectral response for a sample of graphite/epoxy T300/CG914$[0]_{24}$ having delaminations.

FIGS. 6a and 6b show the comparison of leaky Lamb wave reflection spectra for, respectively, defect free and fabricated delaminated plates of graphite/epoxy T300/CG914[0]$_{24}$ tested at 20° along the laminate fibers. Presence of the defect is clearly identified.

Delaminations mechanically decouple the plate into two sections only one of which is excited by the sound beam. This results in a mode pattern characteristic of a thinner plate. By examining the difference in frequency between the modes of the defective material, the depth of the delamination can be inferred. Its spatial extent is determined by noting the area over which the mode structure departs from that of corresponding defect free material. Porosity, by contrast, reduces the excitation of all modes, particularly those at higher frequency. This observation is the basis of a method to distinguish porosity from other defects. For example, FIG. 7 shows a spectral response for a sample of AS43501-6[0]$_{32}$ graphite/epoxy laminate at an incidence angle of 22° and in which porosity was built into the layup by inserting 40 micron diameter hollow glass microspheres between layers of the laminate to simulate known porosity. Close examination of the spectrum of FIG. 7 reveals that the simulated porosity is apparently behaving like a frequency dependent reflector of ultrasound. At low frequenices (long wavelengths), the hollow microspheres are nearly transparent, and as a result, the spectrum is only slightly perturbed in the low frequency region (left end of FIG. 7). In the intermediate frequency range (middle portion of FIG. 7), the reflectivity has increased and the mode structure is therefore substantially suppressed. At high frequencies (short wavelengths), the scatterers are even more effective, and little sound energy penetrates below the microsphere raft within the lamination, resulting in some reestablishment of the mode structure (with minima near 7.5 and 9.0 MHz) appropriate to an effectively thinner plate (i.e., the effective plate thickness between the raft and the upper plate surface).

Examining spectral responses at various frequencies yields additional information on the material condition of the composite, which correspond to other anomalies in the laminate material. A high frequency scan is sensitive to more subtle defects, such as resin-rich regions and fiber orientation. Further, the teachings of the invention may be extended to the examination of curved laminates through consideration of a more complicated relationship between spectral response and incidence angle of ultrasonic energy.

The invention therfore provides a nondestructive evaluation tool by which a large number of defect types in composite materials may be detected and characterized. It is understood that certain modifications to the invention as described may be made, as might occur to one skilled in the field of the invention, within the scope of the appended claims. All embodiments contemplated herein which achieve the objects of the invention have therefore not been shown in complete detail. Other embodiments may be developed without departing from the spirit of the invention or from the scope of the appended claims.

We claim:

1. A system for detecting defects in the structure of a composite laminate material, comprising:
   (a) first transducer means for directing an ultrasonic beam of preselected frequency along a selected transmission axis onto a surface of a laminate material at preselected angle whereby Lamb waves are generated in said laminate material and leaky Lamb waves are reflected from said laminate material;
   (b) second transducer means for receiving said leaky Lamb waves reflected from said laminate material along a reflection axis and for providing an output signal corresponding to the amplitude of the reflected waves received by said second transducer means;
   (c) said first transducer means and said second transducer means each disposed in preselected spaced relationship to each other and spaced from said laminate material such that said transmission axis and said reflection axis intersect within said laminate material at a preselected distance below said surface; and
   (d) fluid means sonically coupling said laminate material and said first transducer means and said second transducer means.

2. The system recited in claim 1 further comprising means interconnecting said first transducer means and said second transducer means in said preselected spaced relationship and means for selectively positioning said first transducer means and said second transducer means along said surface of said laminate material in said preselected spaced relationship.

3. The system recited in claim 2 further comprising electronic means responsive to said signal from said second transducer means for plotting amplitude of said leaky Lamb waves reflected from said laminate material as a function of position of said first transducer means and said second transducer means along said surface of said laminate material.

4. The system recited in claim 1 wherein said fluid means sonically coupling said laminate material and said first transducer means and said second transducer means comprises water.

5. The system recited in claim 4 further comprising means for maintaining respective water columns along said transmission axis and said reflection axis for sonically coupling said laminate material and said first transducer means and said second transducer means.

6. The system recited in claim 1 wherein said preselected frequency is in the range of from about 0.5 to about 15 MHz.

7. The system recited in claim 6 wherein said preselected angle is in the range of from about 8° to about 75° relative to a normal to said surface of said laminated material.

8. A system for detecting defects in the structure of a composite laminate material, comprising:
   (a) a first ultrasonic transducer spaced from a surface of a laminate material for directing an ultrasonic beam of preselected frequency along a transmission axis onto said surface at preselected angle whereby Lamb waves are generated in said laminate material and leaky Lamb waves are reflected from said laminate material;
   (b) a second ultrasonic transducer spaced from said surface and disposed in preselected spaced relationship to said first transducer for receiving said leaky Lamb waves reflected from said laminate material along a reflection axis and for providing an output signal corresponding to the amplitude of the reflected waves received thereby, said transmission and reflection axes intersecting within said laminate material at a preselected distance below said surface;
   (c) means interconnecting said first transducer and said second transducer in said preselected spaced relationship and means for selectively positioning said first transducer and said second transducer along said surface of said laminate material in said preselected spaced relationship;
   (d) electronic means responsive to said signal from said second transducer for plotting amplitude of said leaky Lamb waves reflected from said laminate material as a function of position of said first transducer and said second transducer along the surface of said laminate material; and
   (e) means for maintaining respective water columns along said transmission axis and said reflection axis for sonically coupling said laminate material and said first transducer and said second transducer.

9. The system recited in claim 8 wherein said preselected frequency is in the range of from about 0.5 to about 15 MHz.

10. The system recited in claim 9 wherein said preselected angle is in the range of from about 8° to about 75° relative to a normal to said surface of said laminate material.

11. A method for detecting defects in the structure of a composite laminate material, comprising the steps of:
   (a) providing first and second ultrasonic transducers disposed in preselected spaced relationship to each other and spaced a preselected distance from a surface of said laminate material such that a transmission axis of said first transducer and a reflection axis of said second transducer intersect within said laminate material at a preselected distance below said surface;
   (b) sonically coupling said laminate material and said first transducer and said second transducer;
   (c) directing an ultrasonic beam of preselected frequency along said transmission axis from said first transducer onto said surface of said laminate material at preselected angle whereby Lamb waves are generated in said laminate material and leaky Lamb waves are reflected from said laminate material;
   (d) receiving said leaky Lamb waves reflected from said laminate material along said reflection axis to said second transducer and providing an output signal corresponding to the amplitude of the reflected waves; and
   (e) comparing said output signal with a second signal produced by performing the foregoing steps (c) and (d) using a known defect-free sample of said laminate material.

12. The method recited in claim 11 further comprising the step of selectively positioning said first transducer and said second transducer in said preselected spaced relationship along said surface of said laminate material at said preselected distance, and repetitively performing said steps (c) and (d) at a plurality of positions of said first transducer and said second transducer to produce a corresponding plurality of signals characterizing said laminate material at said plurality of positions.

13. The method recited in claim 12 further comprising the step of plotting the amplitudes of said plurality of said signals as a function of position of said first transducer and said second transducer along said surface of said laminate material.

14. The method recited in claim 11 wherein said preselected frequency is in the range of from about 0.5 to about 15 MHz.

15. The method recited in claim 14 wherein said preselected angle is in the range of from about 8° to about 75° relative to a normal to said surface of said laminate material.

* * * * *

UNITED STATES PATENT AND TRADEMARK OFFICE
CERTIFICATE OF CORRECTION

PATENT NO. : 4,674,334

DATED : June 23, 1987

INVENTOR(S) : Dale E. Chimenti and Yoseph Bar-Cohen

It is certified that error appears in the above-identified patent and that said Letters Patent is hereby corrected as shown below:

Col 3, line 13, "propagagion" should be ---propagation---.

Col 3, line 39, "examiniation" should be ---examination---.

Col 3, line 55, "mainifested" should be ---manifested---.

Col 4, line 7, "efected" should be ---effected---.

Col 5, line 18, "erites" should be ---erties---.

Col 5, line 46, "alternativley" should be ---alternatively---.

Col 6, line 37, "frequenices" should be ---frequencies---.

Col 7, line 58, "laminated" should be ---laminate---.

Signed and Sealed this

Twenty-ninth Day of December, 1987

Attest:

DONALD J. QUIGG

Attesting Officer

Commissioner of Patents and Trademarks